(12) United States Patent
Collazo

(10) Patent No.: US 7,686,533 B2
(45) Date of Patent: Mar. 30, 2010

(54) UNIVERSAL COUPLER

(75) Inventor: Carlos E. Collazo, Old Greenwich, CT (US)

(73) Assignee: Howmedia Osteonics Corp., Mahwah, NJ (US)

( * ) Notice: Subject to any disclaimer, the term of this patent is extended or adjusted under 35 U.S.C. 154(b) by 1455 days.

(21) Appl. No.: 10/972,223

(22) Filed: Oct. 22, 2004

(65) Prior Publication Data

US 2006/0089641 A1    Apr. 27, 2006

(51) Int. Cl.
*F16B 21/02* (2006.01)
(52) U.S. Cl. .......................... 403/325; 24/453; 24/458; 403/240
(58) Field of Classification Search ............. 403/322.1, 403/322–325, 388, 240; 600/417; 606/130; 24/453, 458
See application file for complete search history.

(56) References Cited

U.S. PATENT DOCUMENTS

| 3,145,441 | A | * | 8/1964 | Strandrud .................... 411/347 |
| 3,466,965 | A | * | 9/1969 | McCarthy .................... 411/342 |
| 3,747,168 | A | * | 7/1973 | Snarskis ...................... 411/349 |
| 3,956,803 | A | * | 5/1976 | Leitner ........................ 411/349 |
| 4,372,015 | A | * | 2/1983 | Rhoton ........................ 269/47 |
| 4,696,611 | A | * | 9/1987 | Guay .......................... 411/103 |
| 4,789,287 | A | * | 12/1988 | Le .............................. 411/107 |
| 5,002,547 | A |  | 3/1991 | Poggie |
| 5,443,471 | A |  | 8/1995 | Swajger |
| 5,484,446 | A |  | 1/1996 | Burke |
| 5,499,985 | A |  | 3/1996 | Hein |
| 5,741,263 | A |  | 4/1998 | Umber |
| 5,928,241 | A |  | 7/1999 | Menut |
| 5,935,132 | A |  | 8/1999 | Bettuchi |
| 6,267,543 | B1 | * | 7/2001 | David et al. .................. 411/552 |
| 6,289,557 | B1 | * | 9/2001 | Manson et al. ................ 16/412 |
| 6,659,513 | B1 | * | 12/2003 | Ramsauer ..................... 292/66 |
| 6,732,976 | B2 | * | 5/2004 | Hessling et al. ............. 244/119 |
| 6,893,184 | B2 | * | 5/2005 | Mills et al. ............... 403/322.2 |
| 6,997,658 | B2 | * | 2/2006 | Fly ............................. 411/107 |
| 7,329,066 | B2 | * | 2/2008 | Pineiros et al. ............. 403/353 |
| 2003/0055432 | A1 |  | 3/2003 | Steiger |
| 2003/0163134 | A1 |  | 8/2003 | Riedel |
| 2003/0205903 | A1 | * | 11/2003 | Kelley et al. ................ 292/241 |
| 2004/0010258 | A1 |  | 1/2004 | Carusillo |
| 2006/0179979 | A1 | * | 8/2006 | Dees, Jr. ....................... 81/9.2 |
| 2008/0147075 | A1 | * | 6/2008 | Bonutti ....................... 606/88 |

\* cited by examiner

*Primary Examiner*—Daniel P Stodola
*Assistant Examiner*—Joshua T Kennedy
(74) *Attorney, Agent, or Firm*—Lerner, David, Littenberg, Krumholz & Mentlik, LLP

(57) ABSTRACT

A universal coupler for coupling multiple orthopedic instruments is disclosed. The universal coupler includes a body having a boss and an internal bore, a locking shaft having a first portion and a second portion, a trigger including a trigger bore, and a connection portion. The trigger is operable between a first position and a second position, where in the first position the first portion and boss are misaligned and in the second position the first portion and the boss are aligned.

43 Claims, 11 Drawing Sheets

US 7,686,533 B2

UNIVERSAL COUPLER

FIELD OF THE INVENTION

The present invention relates to the assembly or mating of surgical instruments, and more particularly, to a quick connect universal coupler for allowing the temporary coupling of multiple surgical instruments.

BACKGROUND OF THE INVENTION

Many surgical procedures require the use of orthopedic instruments and ancillary instruments, such as resection guides, gauges, tracking devices, and positioning apparatus. Often times, these various instruments are interactive and need to be assembled and disassembled with each other, thereby requiring some sort of assembly during the surgical procedure. For example, total knee arthroplasty instrumentation frequently requires the use of locating styli or navigation trackers to properly align resection guides. These positioning tools must typically be removably attached to their respective resection guides, to allow for both easy insertion and proper use of the resection guides during surgery.

There have been many attempts at designing coupling means to assemble ancillary instruments, such as tibial and femoral styli, to their counterpart instrument (e.g.—resection guides) during surgery. These means include threaded designs, ball plunger designs and tongue and groove designs. However, problems exist with each of these designs. Threaded designs take significant time to align, turn, and lock. Additionally, applying adequate locking torque to a relatively small screw head is difficult to do with slippery gloves. Ball plunger designs are not ergonomic to use, as they are generally designed to be activated from the top by compressing a spring loaded release button with the thumb, while holding and stabilizing the instrument with the index and middle fingers. If the ancillary instrument is being attached to an instrument already secured to the bone, operating a ball plunger requires the hand to be forced into a partially supinated position that is not optimum from an ergonomic stand point. Finally, tongue and groove designs are used primarily in tibial cutting guides where a slot used for the saw blade is already present. This design is thus limited to instruments that may not be able to accommodate a slot due to size and/or shape constraints.

For the foregoing reasons, there exists a need for a coupler or connector that is quick and easy to utilize.

SUMMARY OF THE INVENTION

A first aspect of the present invention is a universal coupler. The universal coupler according to this aspect includes a body including a boss and an internal bore, a locking shaft including a first portion and a second portion, the second portion disposed within the internal bore of the body, a trigger including a trigger bore for receiving the second portion of the locking shaft, and a connection portion connected to the body for facilitating the connection of the universal coupler to an ancillary instrument. The actuation of the trigger from a first position to a second position moves the locking shaft from a first position in which the locking shaft is misaligned from the boss, to a second position in which the locking shaft is aligned with the boss.

Another embodiment of the present invention is another universal coupler. The universal couple according to this embodiment includes a boss including an internal bore, the boss having a first axis and the internal bore having a second axis, the first axis and second axis being parallel and spaced apart a first distance; a locking shaft including a first portion and a second portion, the first portion having a third axis and the second portion having a fourth axis, the third axis and fourth axis being parallel and spaced apart a second distance, the second portion disposed within the internal bore of the boss and the first distance equal to the second distance; and a trigger assembly including a trigger, the trigger having a trigger bore for receiving the second portion of the locking shaft. The trigger is movable between a first position and a second position, the first position causing the boss and the locking shaft to be misaligned and the second position causing the boss and the locking shaft to align.

Yet another embodiment of the present invention is a coupling system for connecting two parts. The system includes a first part having a bore having an end open to an enlarged portion forming a shoulder between the bore end and the enlarged portion, a second part having a cannulated shaft having an outer surface sized to be received within the bore in the first part, the cannulation in the shaft extending along an axis offset from at least a portion of the outer shaft surface; and a locking element rotatably received within the cannulation, the locking element having a first end with an actuator coupled thereto for rotating the locking element within the second part and a second end having a radially extending flange, the flange having portions spaced from the axis of the cannulation a distance such that rotation of the locking element with the actuator moves the flange from a first position wherein the flange extends beyond a portion of the shaft outer surface into engagement with the shoulder of the first part to connect the first and second parts to a second position wherein the flange is aligned within the shaft outer surface to allow insertion or removal of the shaft from the bore in the first part.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

Figure 1:
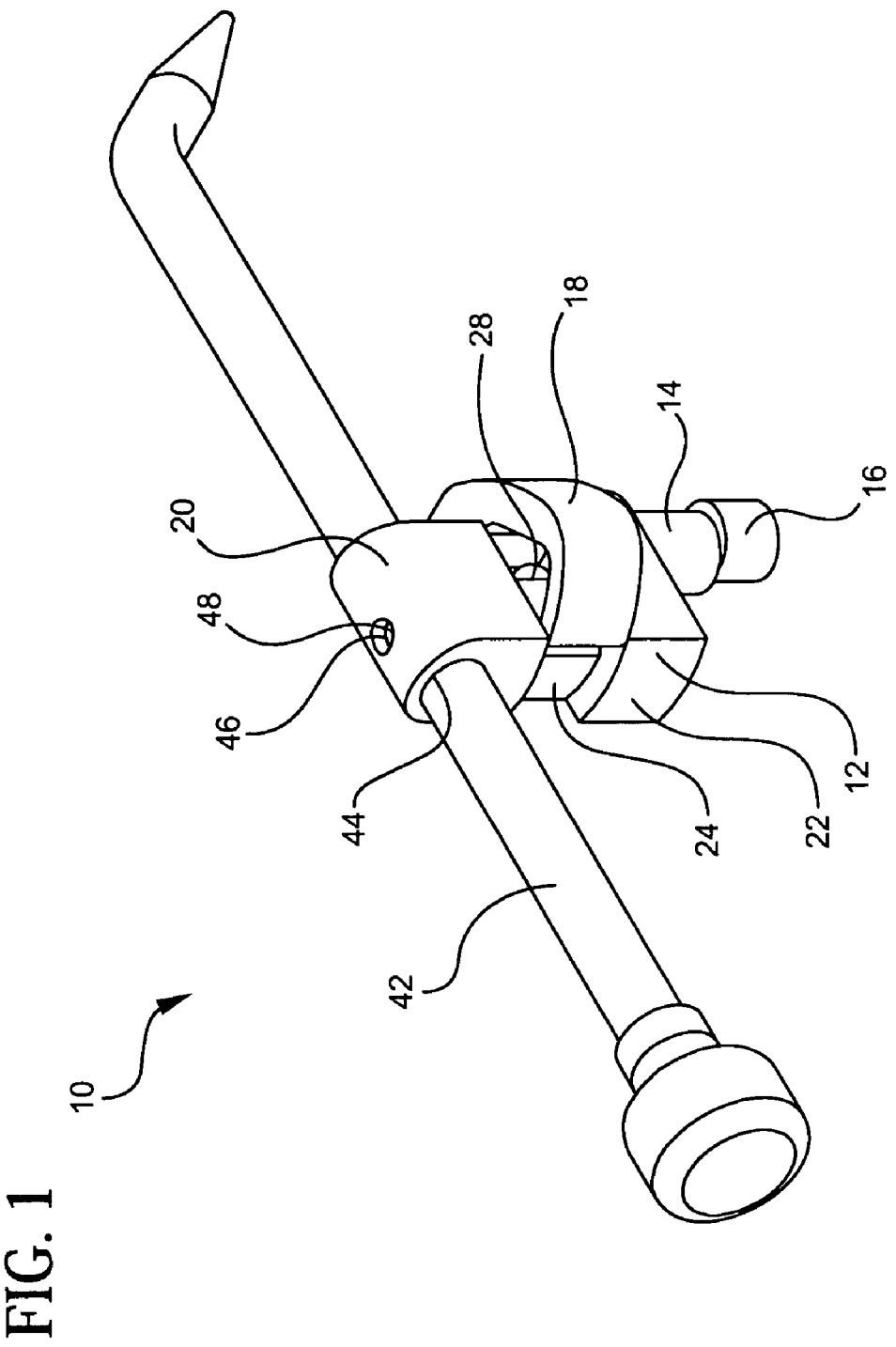
FIG. 1 is a top perspective view of the universal coupler according to an embodiment of the present invention with its trigger in a first position.

In describing the preferred embodiments of the subject matter illustrated and to be described with respect to the drawings, specific terminology will be resorted to for the sake of clarity. However, the invention is not intended to be limited to the specific term and includes all technical equivalence which operates in a similar manner to accomplish a similar purpose.

Referring to the drawings, wherein like reference numerals represent like elements, there is shown in the Figures, in accordance with embodiments of the present invention, a universal coupler designated generally by reference numeral 10. In the embodiment shown in the Figures, coupler 10 is designed to be used in coupling at least two and preferably multiple instruments together in order to perform surgery. For example, as shown in FIGS. 8a-8d respectively, coupler 10 may be used in coupling a patella caliper to a single jaw of a patella resection guide, a navigation tracker adapter to a tibial alignment handle, a femoral stylus to an anterior posterior femoral resection guide, and tibial stylus to a tibial resection guide. While certain instruments are specifically shown being coupled by coupler 10, it is noted that any combination of instruments may be assembled together. As shown in the Figures, coupler 10 includes body 12, cylindrical boss or shaft 14, locking shaft or flange 16, trigger or actuator 18, and connection portion 20.

Figure 2:
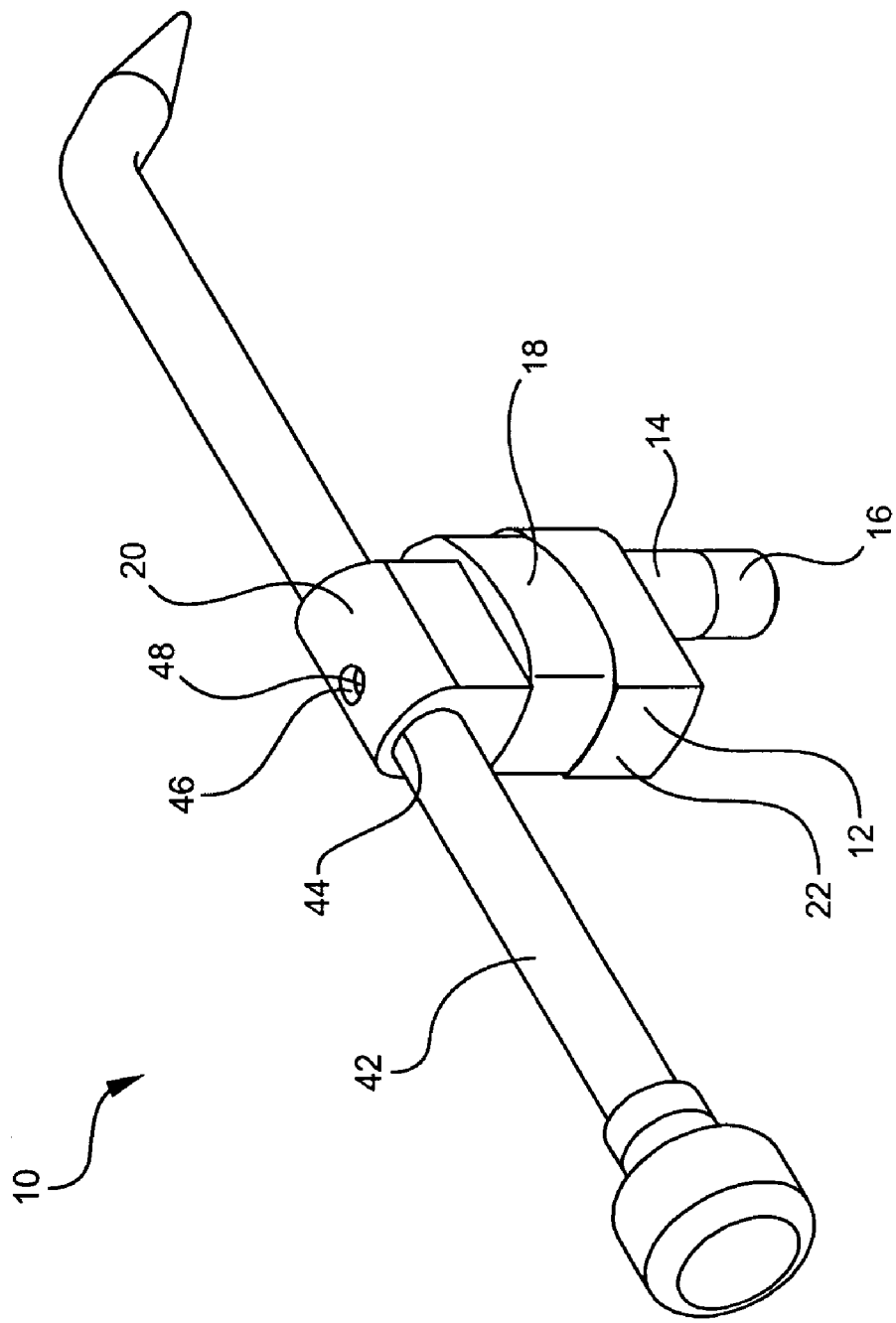
FIG. 2 is a top perspective view of the universal coupler according to FIG. 1 with its trigger in a second position.
Figure 3:
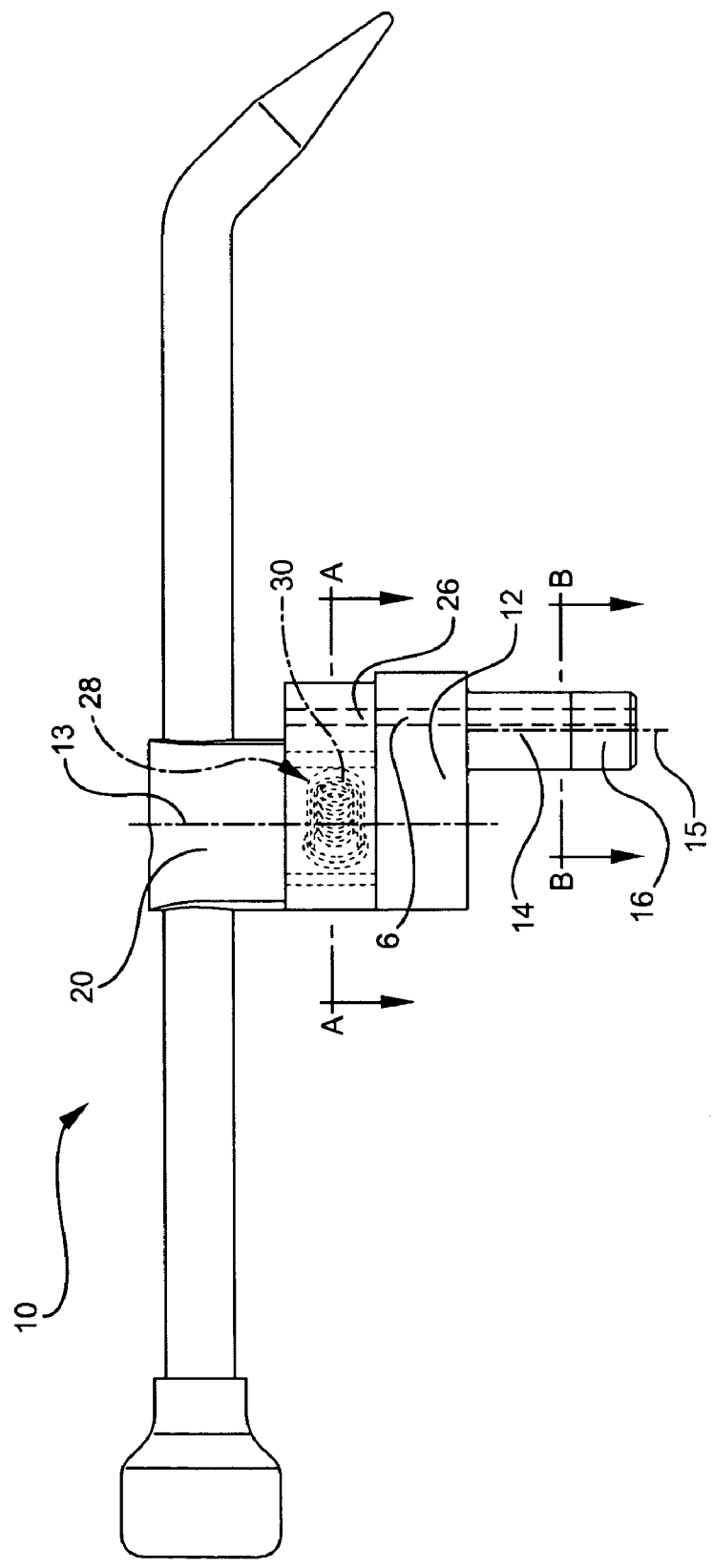
FIG. 3 is a side view of the universal coupler according to FIG. 2 with internal structure being in phantom.

The preferred body 12, as shown in the Figures is substantially rectangular, but may be any shape. Cylindrical boss 14 is a substantially circular tube extending from body 12, and like that of body 12 may be any shape, the only requirement being that its shape must correspond to a hole which it is inserted into. This will be further discussed below. In the embodiment shown in FIGS. 1 and 2, body 12 and cylindrical boss 14 are a single unitary body. However, it is contemplated that other embodiments may include separately constructed pieces that are thereafter mated together by such techniques as welding. As best shown in FIG. 1, body 12 includes main housing 22 and recessed portion 24. Recessed portion 24 is adapted to receive trigger or actuator 18. This will be discussed further below. Further, body 12 also includes internal bore 26 (best shown in FIG. 2) and spring assembly 28. In the preferred embodiment, internal bore or cannulation 26 extends through the entire unitary form created by body 12 and cylindrical boss 14, thus extending through recessed portion 24, main housing 22, and cylindrical boss 14. Internal bore 26 is eccentrically located to a center axis of cylindrical boss 14. As is best shown in FIG. 3, spring assembly 28 includes spring 30 and plunger 32, both of which are housed within counter bore 34. The operation of spring assembly 28 will be discussed below.

Figure 5:
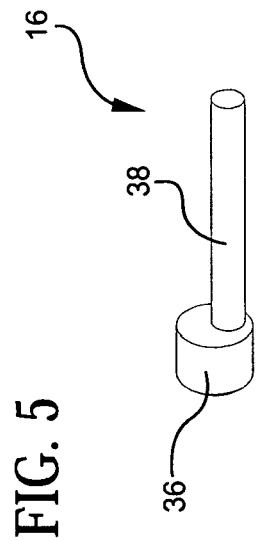
FIG. 5 is a side perspective view of the locking shaft according to FIG. 1.
Figure 6:
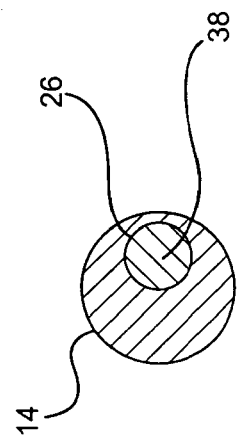
FIG. 6 is a top cross sectional view of section B-B of FIG. 3.
Figure 4:
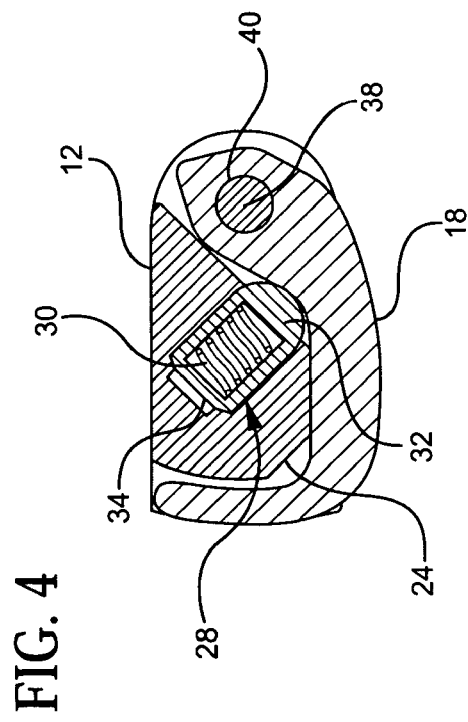
FIG. 4 is a top cross sectional view of section A-A of FIG. 3.
Figure 7:
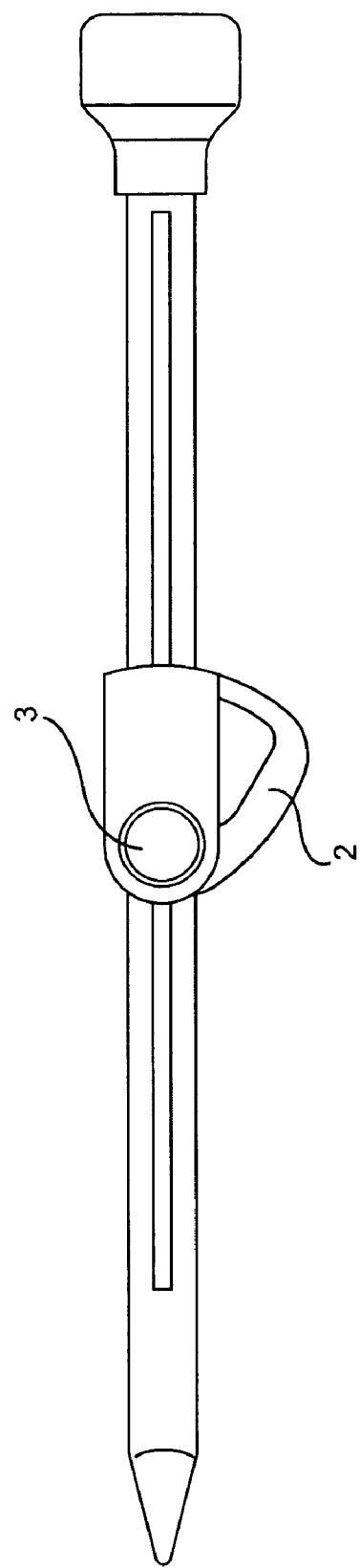
FIG. 7 is a top view of the universal coupler according to FIG. 1.
Figure 8A:
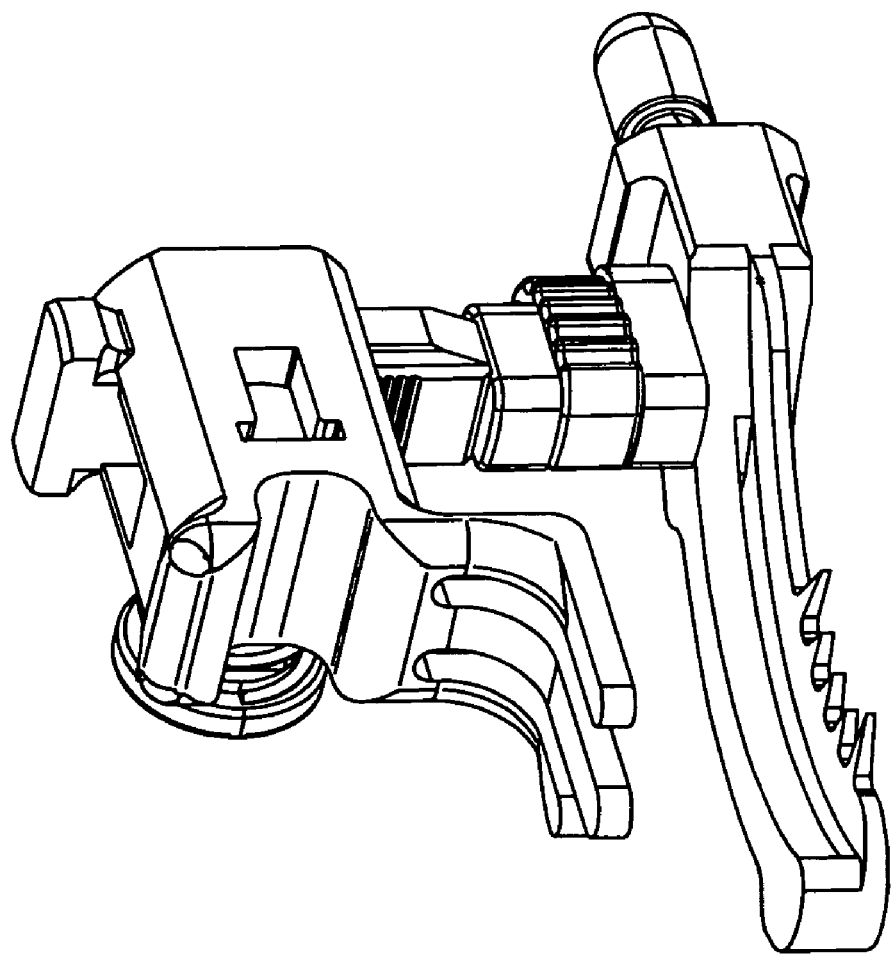
FIGS. 8a-8d depict the universal coupler according to various embodiments of the present invention having different connection portions and connected to different instruments.
Figure 8B:
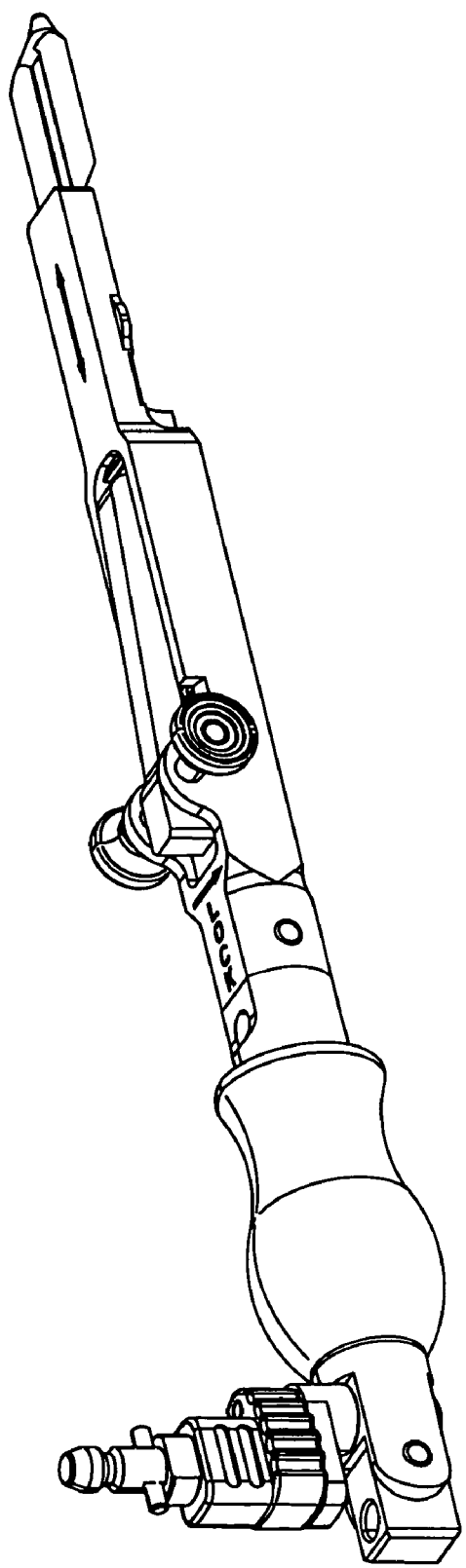
Figure 8C:
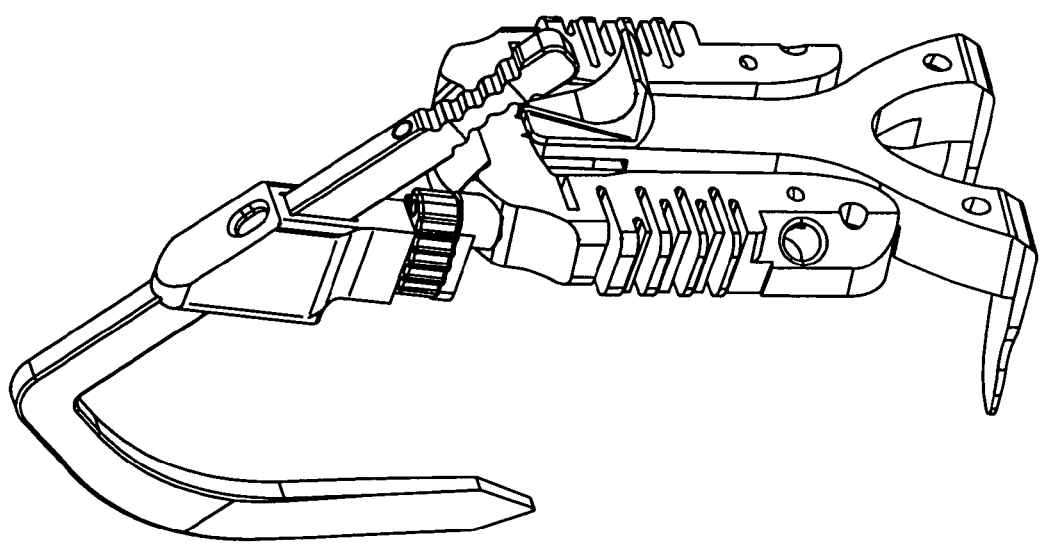
Figure 8D:
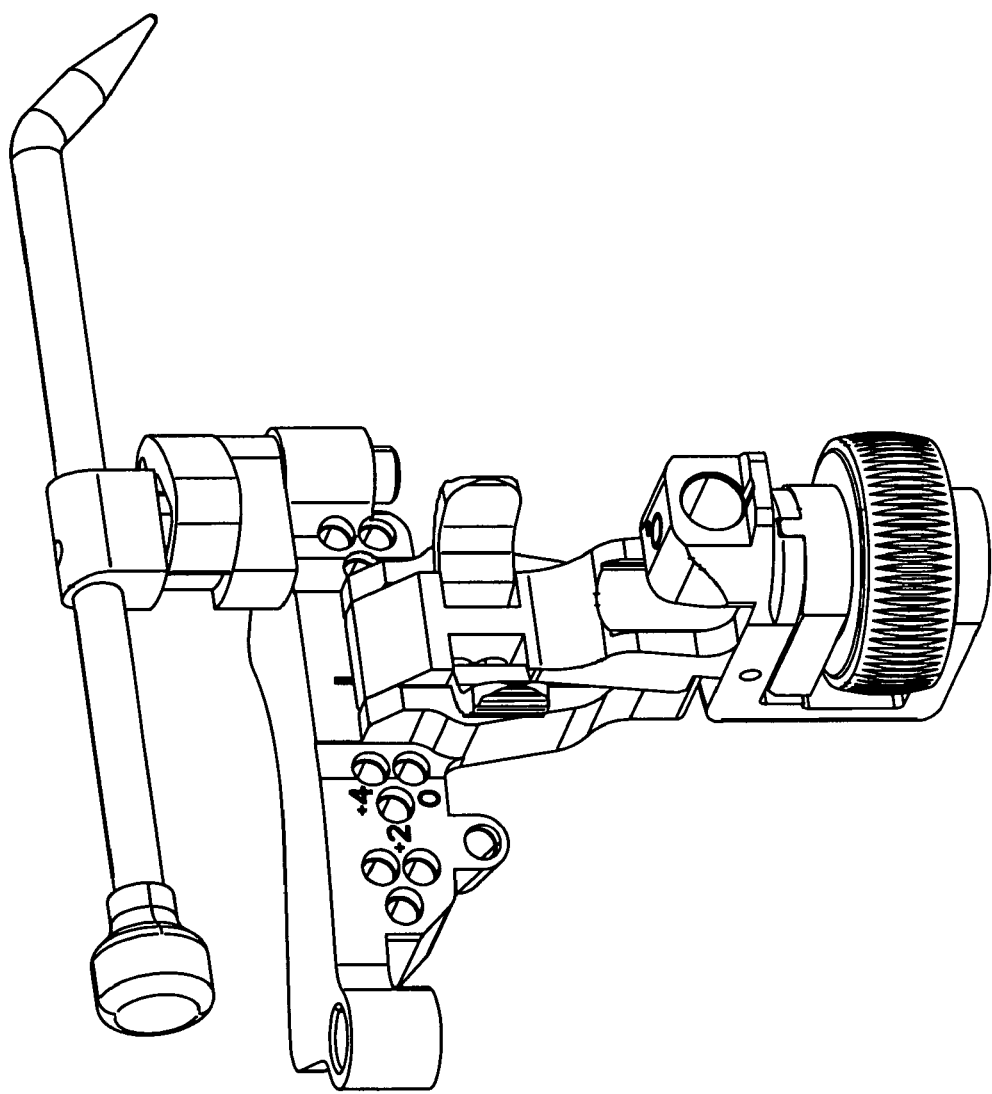

In the preferred embodiment locking shaft 16 includes a first cylindrical portion 36 and a second cylindrical portion 38. This is best shown in FIG. 4. First and second cylindrical portions 36 and 38 are formed integral with one another, however, it is contemplated that they may be formed separately and attached thereafter. First cylindrical portion 36 is typically the same shape and has substantially the same diameter as cylindrical boss 14. Second cylindrical portion 38 is substantially circular, with a diameter slightly smaller than that of internal bore 26. Second cylindrical portion 38 is arranged eccentric to a center axis of first cylindrical portion 36. The distance second cylindrical portion 38 is offset from the center axis of first cylindrical portion 36 is substantially equal to the distance which internal bore 26 is offset from the center axis of cylindrical boss 14. Upon assembly of locking shaft 16 with the remainder of the elements of coupler 10, second cylindrical portion 38 is placed into and through internal bore 26. The cooperation between second cylindrical portion 38 and cylindrical boss 14 is depicted in the cross sectional view of FIG. 5.

As is best shown in FIG. 3, trigger or actuator 18 is a substantially U-shaped member designed to fit within recessed portion 24 of body 12. However, it is contemplated that trigger 18 may be of any shape. Trigger 18 includes trigger bore 40, which is configured and sized to receive the portion of second cylindrical portion 38 that extends through internal bore 26. Essentially, the connection between second cylindrical portion 38 and trigger bore 40 fixably mounts body 12, boss 14, and locking shaft 16 of coupler 10 to one another, while also allowing for the rotation of trigger 18 and second cylindrical portion with respect to body 12.

The assembly of locking shaft 16 and trigger 18 to body 12 and boss 14 should be such that when trigger 18 is in a first position, locking shaft 16 is misaligned from boss 14. This first position is depicted in FIG. 1. The eccentric arrangement of second cylindrical portion 38 with respect to first cylindrical portion 36 allows for the misalignment of locking shaft 16 and boss 14. Essentially, trigger 18 is placed in its first position and attached to locking shaft 16 while the locking shaft is rotated with respect to boss 14. The aforementioned spring assembly 28 is designed and positioned to provide a constant force to trigger 18 and cause the trigger to remain in this first position, absent some sort of counteracting force. Upon application of a counteracting force, trigger 18 is rotated, along with second cylindrical portion 38, into a second position, in which locking shaft 16 and boss 14 are aligned. This position is best shown in FIG. 2.

Connection portion 20 is connected to recessed portion 24 of body 12. As shown in the Figures, connection portion 20 is formed integral with body 12, thus, boss 14, main housing 22, recessed portion 24, and connection portion 20 make up a single unitary body. However, it is contemplated that each element may be formed separately, and thereafter attached to one another. Connection portion 20, as shown in the Figures, is designed and configured to receive and hold a stylus 42. In the embodiment shown, connection portion 20 is substantially rectangular with one rounded side, and includes reception hole 44, bore 46, and spring loaded ball detent 48. Reception hole 44 is adapted to receive a portion of stylus 42, and ball detent 48 is adapted to apply a force thereto to hold stylus 42 in place. In other embodiments, connection portion 20 may include a set screw bore and set screw. In these embodiments, the set screw is adapted, when tightened in the set screw bore, to hold stylus 42 in place. It is contemplated that various other instruments may be connected to coupler 10 by connection portion 20. It is also contemplated that connection portion 20 can be various configurations in order to accommodate the attachment of different instruments. For example, FIG. 7a-7d show different connection portions 20 for receiving and holding different instruments.

Another aspect of the present invention is a method of coupling an ancillary instrument to an orthopedic instrument. The method according to this aspect of the present invention includes the step of providing a universal coupler as discussed above. It is noted that the coupler can be in accordance with any of the various embodiments disclosed herein, as the particular design may not cause the standard method steps to significantly deviate. For the sake of ease in explaining the method, coupler 10 will be utilized herein. The method according to this aspect of the present invention also includes the step of providing an instrument having a mating hole sufficient for receiving coupler 10, such as resection guide 60, as well as an ancillary instrument such as stylus 42.

In another step according to the method, stylus 42 or other ancillary instrument is attached to coupler 10. It is contemplated that this step may be performed prior or subsequent to connecting coupler 10 to an orthopedic instrument. In one preferred embodiment, stylus 42 is connected to coupler 10 prior to attachment of coupler 10 to resection guide 60. In order to connect stylus 42 to coupler 10, a portion of the stylus is inserted into reception hole 44, where ball detent 48 is disposed to hold stylus 42 in place. With stylus 42 attached to coupler 10, trigger 18 is depressed, thereby aligning locking shaft 16 with boss 14 and creating a continuous tubular shaft. This continuous shaft is inserted into a mating hole 50 of resection guide 60, until locking shaft 16 extends beyond hole 50. Thereafter, the continuous force applied to depress trigger 18 is ceased and spring assembly 28 causes trigger 18 to return to its first position. This in turn causes locking shaft or flange 16 and boss 14 to become misaligned, and coupler 10, along with stylus 42, is coupled to resection guide 60. In a preferred embodiment, the preferred offset is approximately 0.042 inches, and the rotation necessary to align flange 16 and boss 14 is approximately 30 degrees. However, it is contemplated that these dimensions can vary in different embodiments. As shown in FIG. 8, coupler 10 includes boss 14 having a diameter D1 and a length L1. Mating hole 50 has a diameter D2 and a length L2. It the embodiment shown, D1 is slightly less than D2 and L1 is slightly longer than L2. This allows for the solid and sturdy connection between the coupler and the instrument.

Figure 9:
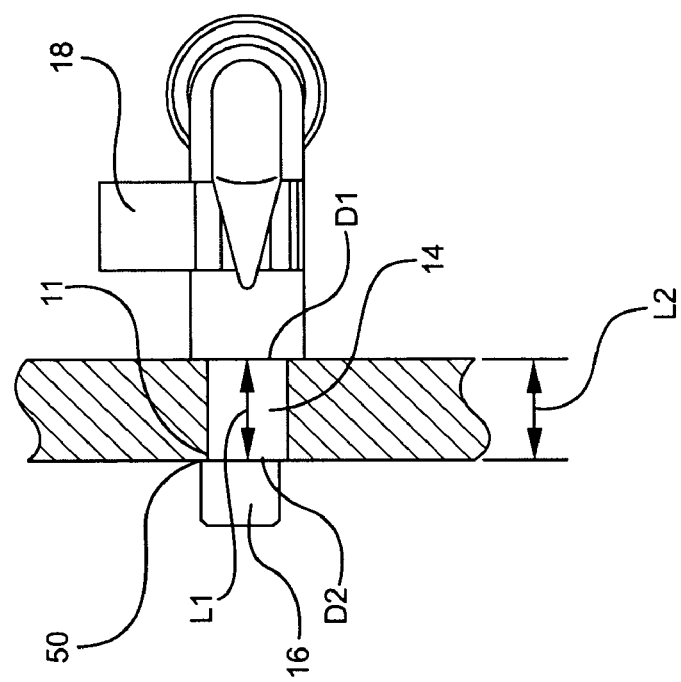
FIG. 9 is a front cross sectional view of the present invention depicting the connection between the universal coupler of FIG. 1 and another instrument.
Figure 10:
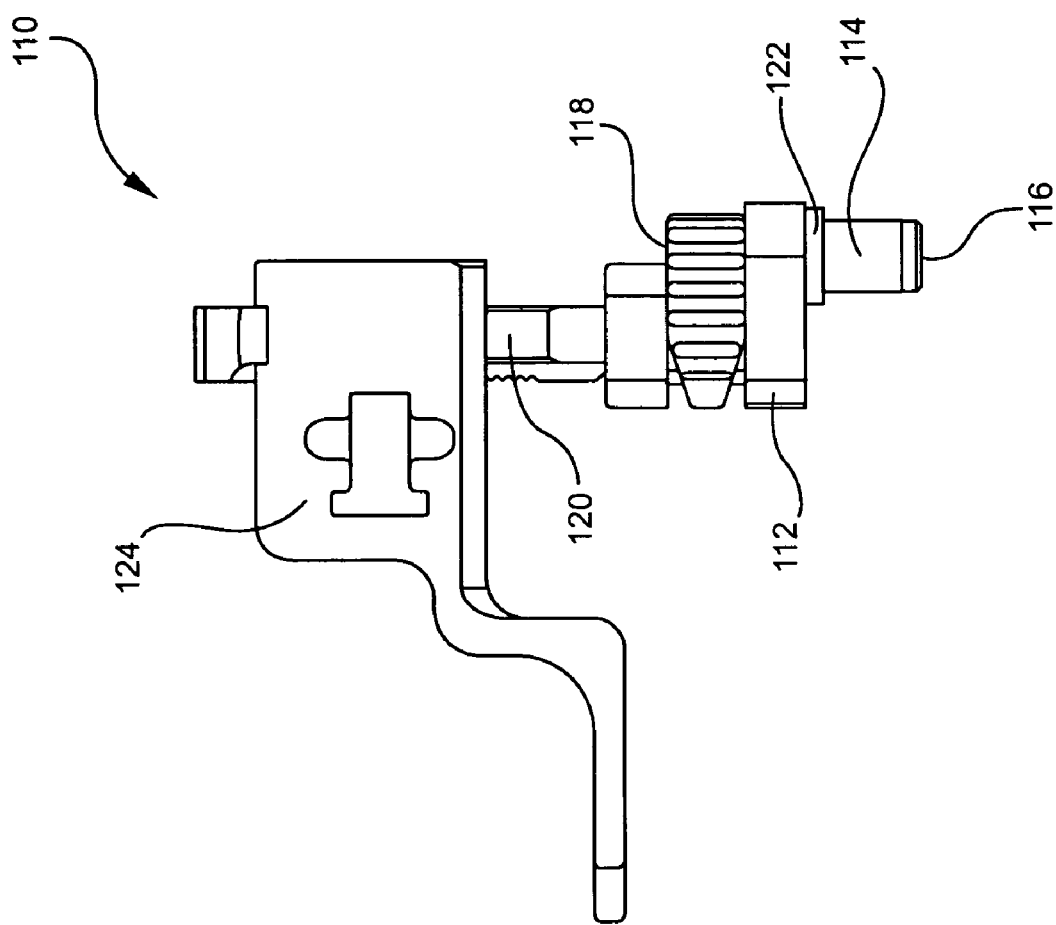
FIG. 10 is a side view of the universal coupler according to another embodiment of the present invention.

FIG. 9 shows another embodiment of the present invention, universal coupler 110. Coupler 110 is substantially similar to coupler 10, except for a different connection portion 120 and the inclusion of rotation locking element 122. Connection portion 120 is configured to allow for the connection and vertical positioning of ancillary instrument 124. Ancillary instrument 124 is a height or thickness gauge for measuring the thickness of a patella, but may be any other type of instrument. Locking element 122 is hexagonal extension extending from body 112 and connected to boss 114. Locking element 122 is designed to fit within a corresponding hexagonal aperture located around a mating hole similar to mating hole 50 discussed above. Upon insertion of coupler 110 into the mating hole having a hexagonal aperture, locking element 122 engages the hexagonal aperture. While the misalignment of locking shaft 116 and boss 114 only prevents removal of coupler 110 from the mating hole, the locking element 122 and hexagonal aperture relationship also prevent the rotation of coupler 110. This is desired in certain situations where both coupling and rotation locking are required. It is contemplated that in other embodiments, locking element 122 may be any shape suitable for preventing rotation of coupler 110. The only requirement being that locking element 122 be configured to mate with a corresponding mating hole. It is also contemplated that rather than including locking element 122, boss 114 and locking shaft 116 may be shaped in order to similarly prevent rotation.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A universal coupler comprising:
a body including a boss having an internal bore therethrough;
a locking shaft including a first portion and a second portion, the first and second portions integrally formed with each other, the second portion disposed within the internal bore of said body;
a trigger rotatably mounted relative to said body and including a trigger body having a bore receiving and rotatably fixing said trigger to the second portion of said locking shaft and a portion extending therefrom; a spring connected to said body biasing said extending portion of said trigger such that said trigger remains in a first, locking position; and
a connection portion connected to said body for facilitating the connection of said universal coupler to an ancillary instrument,
wherein actuation of said trigger from said first, locking position to a second, unlocking position rotates the first and second portions of said locking shaft from a first position in which said first portion is misaligned from said boss, to a second position in which said first portion is aligned with said boss.

2. The universal coupler of claim 1, wherein the boss and the first portion are substantially the same shape.

3. The universal coupler of claim 2, wherein the boss and the first portion are substantially cylindrical.

4. The universal coupler of claim 1, wherein the internal bore and the second portion are substantially the same shape.

5. The universal coupler of claim 4, wherein the internal bore and the second portion are substantially cylindrical.

6. The universal coupler of claim 1, wherein the boss has a first central axis, the internal bore has a second central axis, the first portion has a third central axis, and the second portion has a fourth central axis, the first central axis and the second central axis are parallel and spaced apart a first distance, and the third central axis and fourth central axis are parallel and spaced apart a second distance, the first and second distances being equal.

7. The universal coupler of claim 1, wherein actuation of said trigger causes the first central axis and the third central axis to be coaxial.

8. The universal coupler of claim 7, wherein the boss and the first portion are cylindrical and have substantially equal diameters.

9. The universal coupler of claim 7, wherein the boss and the first portion are non-cylindrical.

10. The universal coupler of claim 7, wherein said trigger is biased to cause the first central axis and the third central axis to be askew.

11. The universal coupler of claim 1, wherein said universal coupler is constructed from a metallic material.

12. An assembly, wherein an instrument is connected to the universal coupler of claim 1.

13. The assembly of claim 12, wherein said instrument is a resection guide.

14. The assembly of claim 12, wherein said instrument is a stylus.

15. The universal coupler of claim 1, further comprising a locking element for the prevention of rotation.

16. The universal coupler of claim 15, wherein the locking element is non-circular.

17. The universal coupler of claim 16, wherein the locking element is hexagonal.

18. A universal coupler comprising:
a boss including an internal bore, said boss having a first central axis and the internal bore having a second central axis, the first central axis and second central axis being parallel and spaced apart a first distance;
a locking shaft including a first portion and a second portion, the first portion having a third central axis and the second portion having a fourth central axis, the third central axis and fourth central axis being parallel and spaced apart a second distance, the second portion disposed within the internal bore of said boss;

a trigger assembly rotatably mounted relative to said boss comprising:

a trigger body, having a trigger bore receiving and rotatably fixing said trigger to the second portion of said locking shaft, a portion extending from said trigger body, and a spring assembly biasing said extending portion of said trigger such that said trigger remains in a first, locking position; and wherein the trigger is movable between said first, locking position and a second, unlocking position, the first position causing the first central axis of said boss and the third central axis of said first portion to be askew and the second position causing the first central axis of said boss and the third central axis of said first portion to be coaxial.

19. The universal coupler of claim 18, wherein said spring assembly further includes a spring plunger.

20. The universal coupler of claim 18, wherein the first distance is equal to the second distance.

21. The universal coupler of claim 18, wherein said boss and the first portion are substantially the same shape.

22. The universal coupler of claim 21, wherein the boss and the first portion are substantially cylindrical.

23. The universal coupler of claim 18, wherein the internal bore and the second portion are substantially the same shape.

24. The universal coupler of claim 23, wherein the internal bore and the second portion are substantially cylindrical.

25. The universal coupler of claim 18, further comprising a connection portion.

26. The universal coupler of claim 18, wherein actuation of said trigger assembly causes rotation of the first and second portions.

27. The universal coupler of claim 18, wherein the boss and the first portion are cylindrical and have equal diameters.

28. The universal coupler of claim 18, wherein said trigger remains in the first position absent a force.

29. The universal coupler of claim 18, wherein said universal coupler is constructed from a metallic material.

30. An assembly, wherein an instrument is connected to the universal coupler of claim 18.

31. The assembly of claim 30, wherein said instrument is a resection guide.

32. The assembly of claim 30, wherein said instrument is a stylus.

33. The universal coupler of claim 18, further comprising a locking element for the prevention of rotation.

34. The universal coupler of claim 33, wherein the locking element is non-circular.

35. The universal coupler of claim 33, wherein the locking element is hexagonal.

36. A coupling system for connecting two parts, said system comprising:

a first part having a first bore having an end open to an enlarged portion forming a shoulder between said first bore end and said enlarged portion;

a second part having a shaft having a second bore and an outer surface sized to be received within said first bore in said first part, said second bore in said shaft extending along an axis offset from at least a portion of said outer shaft surface; and a locking element rotatably received within said second bore, said locking element having a first end with a biased actuator coupled thereto for rotating said locking element within said second part and a second end having a radially extending flange, said flange having portions spaced from the axis of said second bore a distance such that rotation of said locking element with said actuator moves said flange from a first position wherein said flange extends beyond a portion of said shaft outer surface into engagement with said shoulder of said first part to connect said first and second parts to a second position wherein the flange is aligned within said shaft outer surface to allow insertion or removal of said shaft from said first bore in said first part wherein said locking element is biased towards said first position.

37. The coupling system as set forth in claim 36 wherein said biasing is provided by a coil spring acting on said actuator.

38. The coupling system as set forth in claim 36 wherein said locking element is a rod and said flange is circular and coupled to an end of said rod wherein a central axis of the rod is offset from a central axis of the flange.

39. The coupling system as set forth in claim 38 wherein said shaft is circular and wherein the axis of said second bore in said shaft is offset from a central axis of said circular shaft.

40. The coupling system as set forth in claim 39 wherein said shaft is rotatable within said first bore.

41. The coupling system as set forth in claim 40 further comprising means for rotationally locking said shaft within said first bore.

42. The coupling system as set forth in claim 36 wherein said enlarged portion is a bottom surface of a plate.

43. The coupling system as set forth in claim 36 wherein said flange has portions spaced from said second axis a distance equal to the offset between said axis and said portion of said shaft outer surface.

\* \* \* \* \*